United States Patent
Veeraraghavan et al.

(10) Patent No.: US 8,768,665 B2
(45) Date of Patent: Jul. 1, 2014

(54) SITE BASED QUANTIFICATION OF SUBSTRATE TOPOGRAPHY AND ITS RELATION TO LITHOGRAPHY DEFOCUS AND OVERLAY

(75) Inventors: Sathish Veeraraghavan, Santa Clara, CA (US); Jaydeep Sinha, Livermore, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 1086 days.

(21) Appl. No.: 12/778,013

(22) Filed: May 11, 2010

(65) Prior Publication Data

US 2011/0172982 A1     Jul. 14, 2011

Related U.S. Application Data

(60) Provisional application No. 61/293,548, filed on Jan. 8, 2010.

(51) Int. Cl.
*G06G 7/48* (2006.01)
*G06F 17/50* (2006.01)

(52) U.S. Cl.
CPC .................. *G06F 17/5009* (2013.01)
USPC .......................................................... 703/6

(58) Field of Classification Search
CPC . G06F 17/5022; G06F 17/50; G06F 17/5009; G06F 17/5068; G06F 17/5081; G06F 17/5018; G03F 1/36; G03F 7/705; G03F 1/44; G03F 1/84; G03F 7/70825
USPC ................... 703/13, 1, 2, 6; 430/325; 73/105; 716/54, 51, 52, 53, 112, 55, 111, 56; 438/14; 702/167
See application file for complete search history.

(56) References Cited

FOREIGN PATENT DOCUMENTS

WO     WO2010/025334 A1     3/2010

OTHER PUBLICATIONS

T. D. Raymond, D. R. Neal, and D. M. Topa, "High-speed, non-interferometric nanotopographic characterization of Si wafer surfaces," SPIE 4809-34 (2002).*
Kevin M. Monahan ; Patrick J. Lord ; Clive Hayzelden ; Waiman Ng; Application of model-based lithographic process control for cost-effective IC manufacturing at 0.13 μm and beyond. Proc. SPIE 3677, Metrology, Inspection, and Process Control for Microlithography XIII, 435 (Jun. 14, 1999).*
K. Turner et al, "Predicting Distortions and Overlay Errors Due to Wafer Deformation During Chucking on Lithography Scanners", J. Micro/Nanolith, MEMS MOEMS 8(4), 043015, (Oct.-Dec. 2009), 8 Pages.
J. Valley et al, "Approaching New Metrics for Wafer Flatness: An Investigation of the Lithographic Consequences of Wafer Non-Flatness", Proceedings of SPIE, 5375, 1098 (2004), 11 Pages.
K. Freischlad et al, "Interferometry for wafer dimensional metrology", Proceedings of SPIE, 6672, 1 (2007), 14 pages.

* cited by examiner

*Primary Examiner* — Kamini S Shah
*Assistant Examiner* — Luke Osborne
(74) *Attorney, Agent, or Firm* — Suiter Swantz pc llo

(57) ABSTRACT

A method and system for modeling and analyzing wafer nanotopography data utilizes a nonlinear contact finite element model. Inputs to the model include lithography chuck parameters and site-based geometry data. Outputs from the model include in-plane distortions and out-of-plane distortions, from which defocus and overlay can be derived.

21 Claims, 11 Drawing Sheets

Bending Deformation Assumption $$\varepsilon_{front} \approx -\frac{d^2 z_{NT}}{dx^2}\frac{h}{2} = \frac{\pi^2}{2}\frac{Ah}{L^2}\sin\left(\pi\frac{x}{L}\right)$$

$$\varepsilon_{front}\big|_{max} \approx \frac{\pi^2}{2}\frac{Ah}{L^2}$$

A – amplitude of topography
h – thickness (775 µm)
L – spatial wavelength of topography

| Case 1 | Case 2 |
|---|---|
| Front Surface Before Chucking (PV ~ 6 nm) | Front Surface Before Chucking (PV ~ 5 nm) |
| 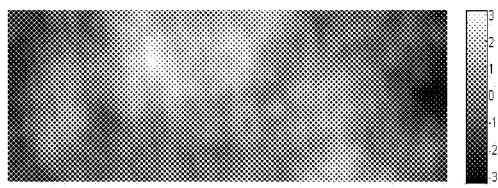 | 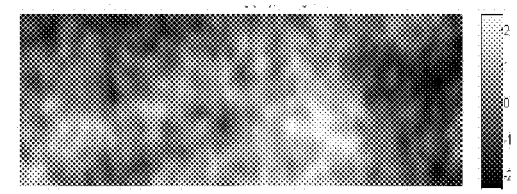 |
| Back Surface Before Chucking (PV ~ 4 nm) | Back Surface Before Chucking (PV ~ 13 nm) |
| 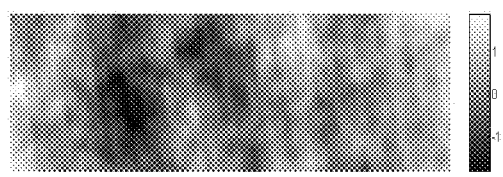 | 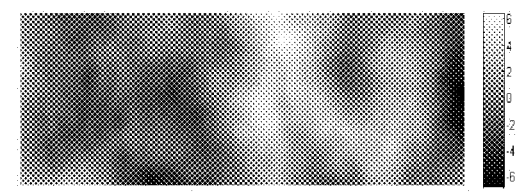 |
| Front Surface After Chucking (PV ~ 6 nm) | Front Surface After Chucking (PV ~ 13 nm) |
| 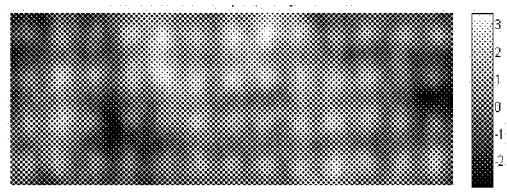 | 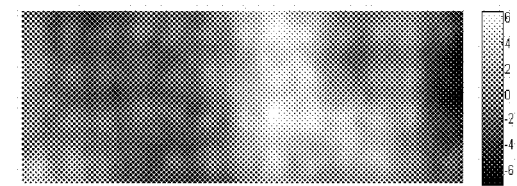 |
FIG. 7a  FIG. 7b Back Surface Before Chucking (PV ~ 4 nm)

Back Surface Before Chucking (PV ~ 13 nm)

IPD on Front Surface (IPDmax = 0.2 nm)

IPD on Front Surface (IPDmax = 1.2nm)

SITE BASED QUANTIFICATION OF SUBSTRATE TOPOGRAPHY AND ITS RELATION TO LITHOGRAPHY DEFOCUS AND OVERLAY

CROSS-REFERENCE TO RELATED APPLICATIONS

This application is related to U.S. Provisional application No. 61/293,548, filed Jan. 8, 2010, and claims priority thereto.

FIELD OF THE INVENTION

This invention relates to integrated circuit processing, and in particular to the characterization of wafer substrate topography and its relation to overlay and defocus errors in lithography.

BACKGROUND

As integrated circuits become faster and denser, requirements for lithography become increasingly stringent. Errors in lithography can result from in-the-plane distortions (which can result in overlay errors) or from out of the plane distortions, which can result in defocus. The necessity for verifying that a given wafer is sufficiently planar and within specifications, i.e. in qualifying and selecting wafers even before processing begins or during processing, is becoming ever greater. A critical component in the characterization of wafers is the wafer topography, sometimes termed substrate geometry.

Wafer topography (i.e., substrate geometry) can be described according to traditional parameters such as shape, thickness/flatness, and nanotopography (NT). These parameters have different characteristics, as is illustrated in FIG. 1a. The data representing these parameters have a high spatial resolution of about 0.2 mm. Shape is defined as the median surface of the substrate (as in the deviation of the median surface from a reference plane), generally in a free state, and is a low frequency component of the wafer. Shape is characterized by global metric such as warp and bow. Flatness is defined as the thickness variation of a substrate with the back surface assumed to be completely flat, and is characterized by metrics, which may be localized or site-based. Characterization and quantification of higher order components of shape and more localized shape features are described in PCT publication No. WO 2010/025334, and U.S. Provisional application No. 61/092,720, both of which are incorporated by reference in their entireties. The impacts of the wafer shape on lithography parameters are described in K. Turner et al, "*Predicting Distortions and Overlay Errors Due to Wafer Deformation During Chucking on Lithography Scanners*", J. Micro/Nanolith, MEMS MOEMS 8(4), 043015, (October-December 2009), and the impacts of flatness on lithography parameters are described in J. Valley et al, "*Approaching New Metrics for Wafer Flatness: An Investigation of the Lithographic Consequences of Wafer Non-Flatness*", Proceedings of SPIE, 5375, 1098 (2004) which is hereby incorporated by reference in its entirety.

In particular, higher order components of wafer shape and NT, as illustrated in FIG. 1b, might influence both overlay, i.e. registration or alignment between lithography levels, and defocus. Nanotopography is the high frequency component of the front and back surface of the substrate, defined as being in a spatial wavelength regime of 0.2-20 mm, and with a feature height of a few nanometers. NT may occur as point defects (e.g., dimples, epi defects such as pins or crowns, bumps such as notches or lasermarks) or as line defects (e.g., saw marks from slicing, scratches, slip lines, dopant striation or other process signatures). The individual front/back surface nanotopography of a wafer substrate is typically obtained from the front/back topography by applying high pass filtering schemes such as Double Gaussian (DG) filtering to the topography data, which suppresses the low frequency components of the wafer topography. The substrate NT parameters are seen to affect the lithography process, for example by contributing to defocus and overlay errors.

Typically, in lithographic processing, corrections to distortions or other topographic features which may result in overlay or defocus errors are applied by the scanner on both a full wafer-level and a site-by-site basis. The most common linear scanner corrections (which includes both wafer level and site level) for overlay are: translation in x and y, rotation, and site-level magnification in xy and y. The corrections in x and y typically have the mathematical form:

$$dx = \Delta x - \Delta \theta \cdot y + MX \cdot x$$

$$dy = \Delta y - \Delta \theta \cdot x + MY \cdot y$$

where $\Delta x$ and $\Delta y$ are the shifts in x and y, $\Delta \theta$ is the rotation correction, and MX and MY are the magnification corrections in x and y. The corrections are typically calculated by minimizing the errors at target locations within the lithography sites using a process such as least squares.

Scanner based linear corrections can generally correct for lower order linear components of the substrate geometry and other linear components which might result in overlay and defocus errors. However, typically the lithography scanner has limited capability to correct for features with spatial frequency less than 1/slit size of the lithography scanner. The NT which has spatial frequency less than 1/slit size may therefore result in Non-Correctable Errors (NCE).

SUMMARY OF THE INVENTION

A methodology and system therefore is presented herein for quantifying the substrate NT and its effect on the lithography process parameters. This methodology utilizes a finite element model.

BRIEF DESCRIPTION OF THE DRAWINGS

FIG. 7a shows exemplary FE modeling results of the effects of backside NT on frontside topography while chucked, for a first case.

FIG. 7b shows exemplary FE modeling results of the effects of backside NT on frontside topography while chucked, for a second case.

DETAILED DESCRIPTION

Figure 1A:
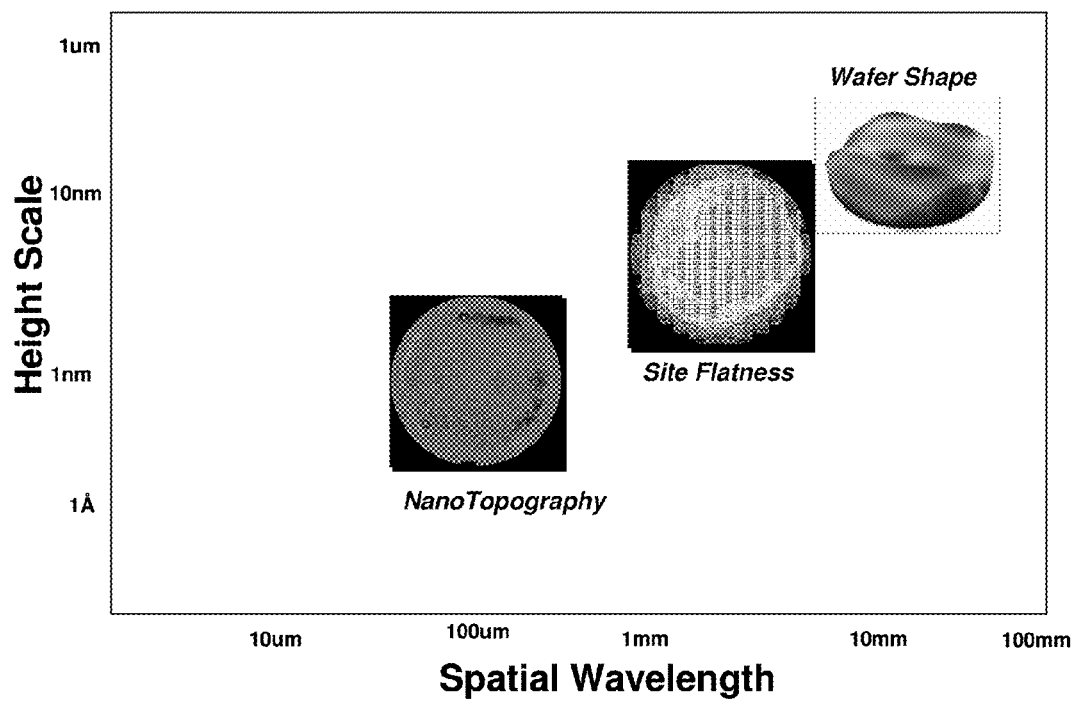
FIG. 1a characterizes different parameters of substrate geometry/wafer topography.
Figure 1B:
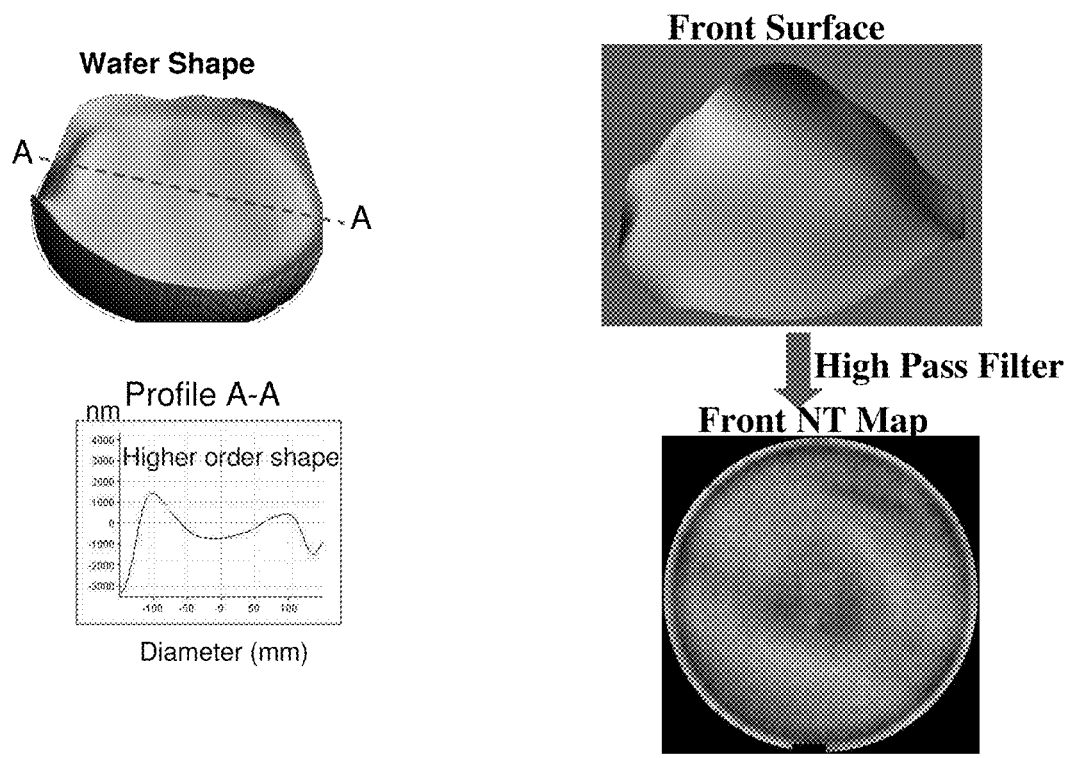
FIG. 1b illustrates higher order shape and nanotopography.

The method and system described herein provides for the measurement and quantification of wafer NT relevant to lithography with appropriate metrics (such as Peak-to-Valley (PV) range and RMS), and the effect of the NT on such parameters as lithography defocus and overlay error. The results obtained in this way enable the sorting and/or qualification of bare or patterned wafers for the process flow. Wafer qualification may be accomplished by comparing the quantified metric values to a user-determined threshold or cut-off, which may be determined at least in part by the process flow.

A first requirement for developing a quantification methodology for determining the influence of wafer topographical aspects such as NT or shape on lithographic overlay/defocus is to accurately measure the wafer front and back surface topography. Wafer measurement with the wafer in a free state, where front and back surface an be measured simultaneously, is preferred, since it eliminates possible artifacts in the substrate topography data due to the interaction between the substrate and the chuck or other holding mechanism.

A dimensional metrology tool such as WaferSight2 from KLA-Tencor provides the utility of measuring front-side and back-side topography, as well as thickness/flatness, simultaneously. This tool is described in K. Freischlad, S. Tang, and J. Grenfell, "*Interferometry for wafer dimensional metrology*", *Proceedings of SPIE*, 6672, 1 (2007), which is hereby incorporated by reference in its entirety. An aspect of the improved measurement methodology provided by this tool is that the substrate is measured in a free state, where the substrate is held vertically at only a few contact points, so that the topography of the front and back surface can be measured simultaneously. Use of the WaferSight2 tool enables refinement of quantification methodology for NT. Note that measurements of the wafer topography may be stored in computer memory, and computer-based analysis and/or modeling may be performed.

The inventive quantification methodology is site-based, which generally implies localized. Prior methodologies for NT, a surface-based quantity, provided one "average" or threshold curve for the entire wafer. In contrast, flatness/thickness measurement and characterization, as well as shape measurement and characterization, have been previously addressed by more sophisticated site-based methods, as described in previously incorporated PCT publication no. WO 2010/025334, and in SEMI M49-0307, "Guide for specifying geometry measurement systems for silicon wafers for the 130 nm-65 nm node technology", *Semiconductor Equipment and Materials International (SEMI)*, 2004. As design rules get smaller, presently reaching approximately 22 nm, the impact of high frequency NT features on lithography parameters such as defocus/overlay increases. Accordingly, it becomes increasingly important to refine the measurement quantification methodology for NT and to develop process-relevant metrics. Site-based measurement methods have two important advantages over whole-wafer averaging methods:

1. Large local deviations are given more weight, rather than being averaged out;
2. The sites may be chosen to correspond to the fields (sites) of the lithography scanner, (a typical lithography site may be 26 mm×8 mm), thus enabling direct correlation between the NT and overlay error on the lithography scanner. The sites are user-defined, but choosing them to correspond to the lithography fields yields substantial advantages. The ability to quantify NT for each lithography field, for example, is relevant for final yield computation.

An embodiment of the present NT quantification method calculates the substrate geometry in a way compatible with the calculation of defocus and overlay errors in each lithography field, also termed "sites". Therefore the substrate geometry may be quantified in the lithography field domain to correlate with the defocus and overlay.

An embodiment of the present method uses the site-based quantification methodology, and utilizes a non-linear contact finite element modeling scheme to model the effects of the NT on In-Plane-Distortion (IPD), from which overlay can be derived. Use of finite element modeling to model the effects of wafer shape distortion on overlay errors is described in the previously incorporated paper by K. Turner et al.

A brief description of Finite element analysis is as follows:

FEA consists of a computer model of a material or design that is stressed and analyzed for specific results. It is used in new product design, and existing product refinement. A company is able to verify a proposed design will be able to perform to the client's specifications prior to manufacturing or construction. Modifying an existing product or structure is utilized to qualify the product or structure for a new service condition. In case of structural failure, FEA may be used to help determine the design modifications to meet the new condition.

There are generally two types of analysis that are used in industry: 2-D modeling, and 3-D modeling. While 2-D modeling conserves simplicity and allows the analysis to be run on a relatively normal computer, it tends to yield less accurate results. 3-D modeling, however, produces more accurate results while sacrificing the ability to run on all but the fastest computers effectively. Within each of these modeling schemes, the programmer can insert numerous algorithms (functions) which may make the system behave linearly or non-linearly. Linear systems are far less complex and generally do not take into account plastic deformation. Non-linear systems do account for plastic deformation, and many also are capable of testing a material all the way to fracture.

FEA uses a complex system of points called nodes which make a grid called a mesh. This mesh is programmed to contain the material and structural properties which define how the structure will react to certain loading conditions. Nodes are assigned at a certain density throughout the material depending on the anticipated stress levels of a particular area. Regions which will receive large amounts of stress usually have a higher node density than those which experience little or no stress. Points of interest may consist of: fracture point of previously tested material, fillets, corners, complex detail, and high stress areas. The mesh acts like a spider web in that from each node, there extends a mesh element to each of the adjacent nodes. This web of vectors is what carries the material properties to the object, creating many elements. (Theory)

A wide range of objective functions (variables within the system) are available for minimization or maximization:

Mass, volume, temperature
Strain energy, stress strain
Force, displacement, velocity, acceleration
Synthetic (User defined)

FEA may be implemented using a commercially available modeling package such as ANSYS. The choice of inputs and outputs to/from the modeling package is critical in obtaining maximum utility from the modeling. In an embodiment, the model is generated using a series of custom MATLAB scripts that read the high-density NT data files and construct the model geometry and mesh for the FE package.

Figure 2:
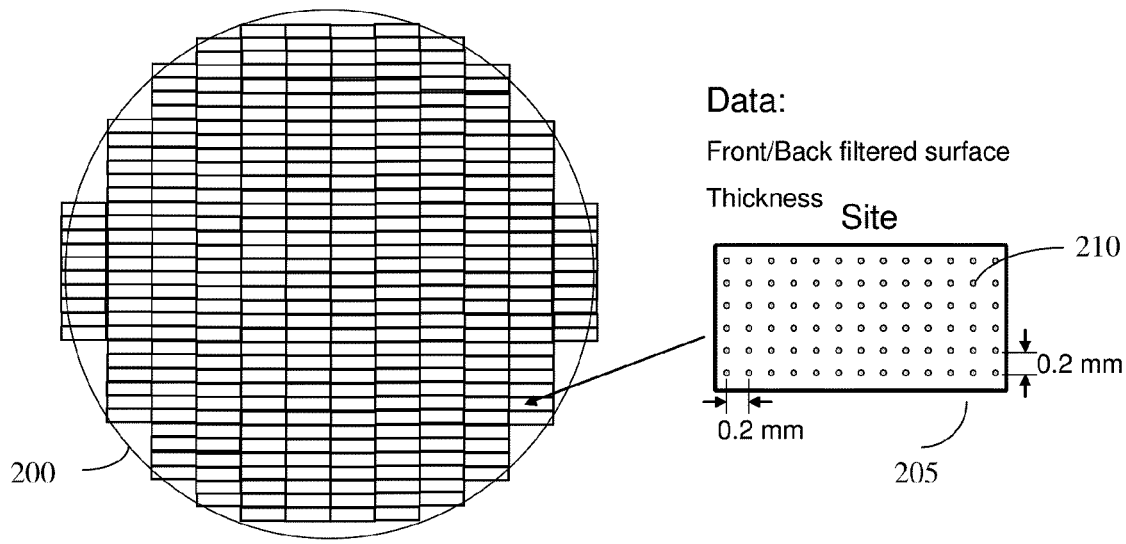
FIG. 2 illustrates the dividing of the wafer into lithography fields or sites.
Figure 3A:
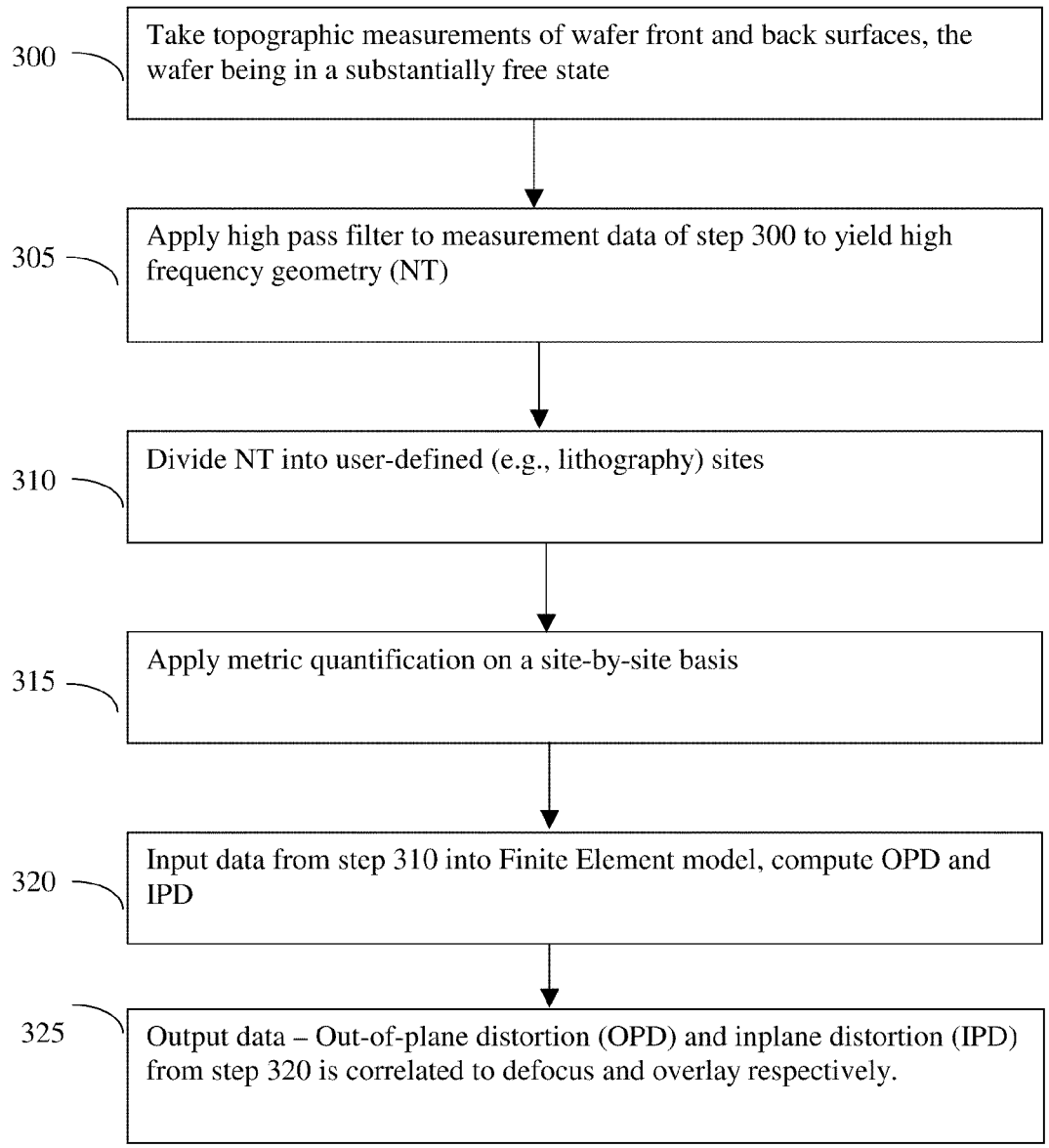
FIG. 3 is a high level flow diagram of an embodiment of a method for quantifying substrate NT.
Figure 3B:
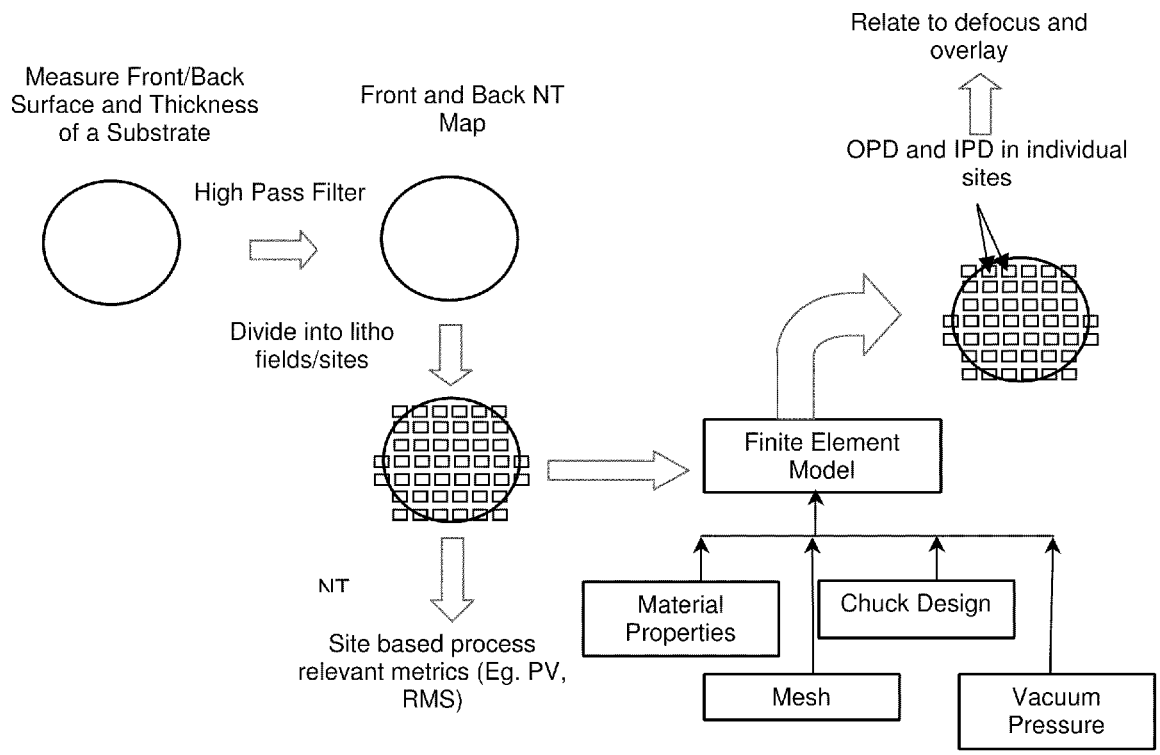

An embodiment of a method for quantifying substrate NT according to the above domain structure includes dividing the substrate surface into lithography fields (sites) and then quantifying the measured NT in each lithography field using an appropriate metric such as a range, deviation, or root mean square (RMS). By way of example, the maximum magnitude of NT features may be quantified using a range metric, whereas to quantify the average high frequency NT, RMS may be utilized. FIG. 2 illustrates wafer 200 divided into lithography fields or sites 205. Within each site, substrate front and back surface filtered geometry data points 210 are taken with an exemplary density of 0.2 mm in x and y. The data may include NT and/or thickness data. FIG. 3a shows a high level flow diagram of this method embodiment: In step 300, topographic measurements are performed on the wafer front and back surfaces, the wafer being in a substantially free state. In step 305, a high pass filter is applied to measurement of the front or back substrate surface. In step 310, the remaining surface features, i.e., the high frequency geometry or NT, is divided into user-defined sites such as lithography sites. In step 315, metric quantification is applied on a site-by-site basis. In step 320, the data obtained in this way is input into the Finite Element model and out of plane distortions (OPD) and IPD are computed. In step 325, data is output, and the OPD and IPD from step 320 are correlated to defocus and overlay respectively. FIG. 3b is a visual illustration of the flow diagram of FIG. 3a. Once the substrate NT is quantified on a site-by-site basis, in a method embodiment, non-linear contact Finite Element Analysis (FEA) is used to model the effect of the NT on the lithography parameters. In particular, during lithographic exposure, the wafer is held on a vacuum chuck against pins. The chucking procedure substantially flattens the back side of the substrate during chucking, which results in bending and shear deformation. In order to determine the effects on the lithographic errors such as defocus and overlay errors, the wafer topography during the chucking process needs to be determined. Note that chucking may also occur during processes such as epitaxial deposition and CMP, as well as during wafer scanning. The methods described herein can also be applied to these other situations. The non-linear contact Finite Element Model models the interaction of the substrate back surface including NT with the chuck, e.g., lithography pins. Note that the FEA can be used to model different parameters such as substrate shape. Depending on the parameter under study, the inputs to the model are varied, as described below.

Figure 4:
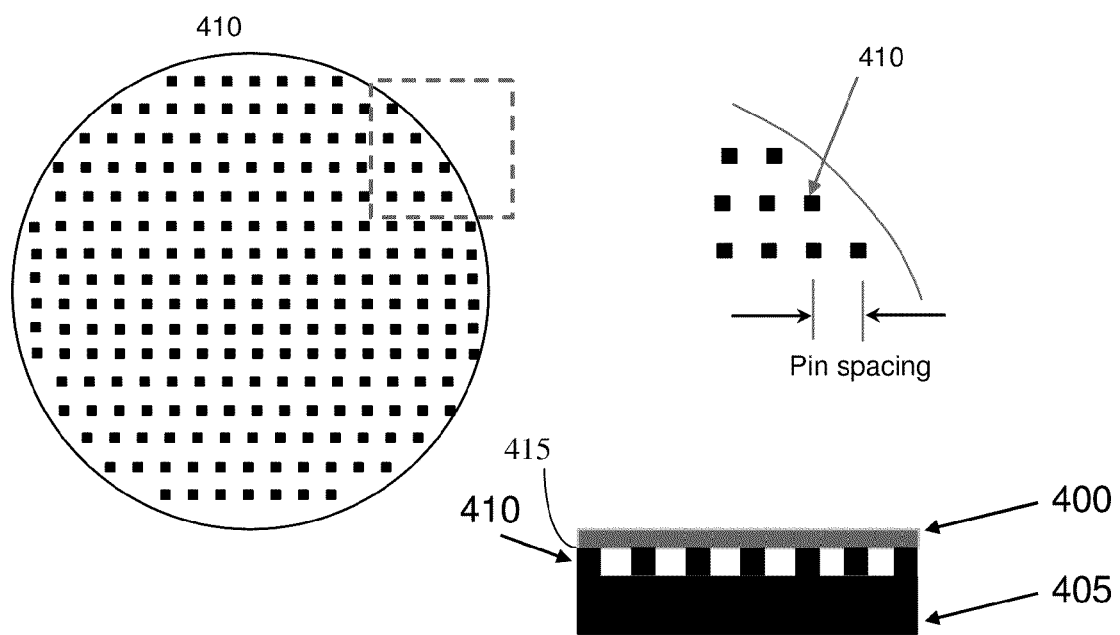
FIG. 4 illustrates the chucking of a wafer.

In the present system, an important input to the model is the interaction of the wafer backside with the pins used when the wafer is vacuum chucked, such as during a scanning or a lithography step. For simplicity, the pins used for vacuum chucking the wafer will be referred to as lithography pins. FIG. 4 illustrates the chucking of wafer 400 on chuck 405, with pins 410 contacting wafer back surface 415.

Figure 5:
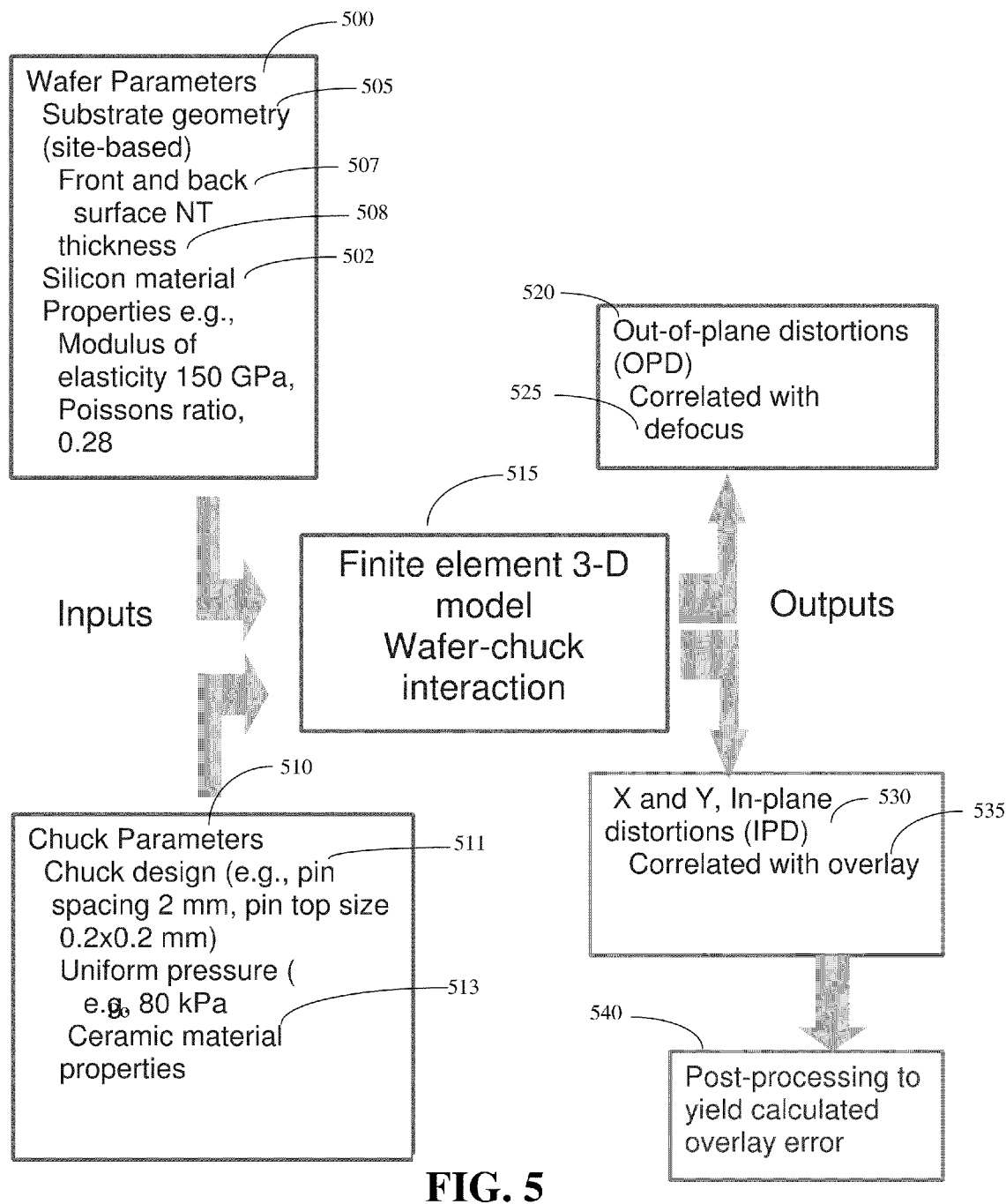
FIG. 5 illustrates a high level diagram of the finite element model used herein.

FIG. 5 illustrates a high level diagram of a finite element model embodiment used herein. Wafer parameters 500 are a first input category to the finite element model 515. Wafer parameters include: a) Silicon material properties 502 (for example, modulus of elasticity, e.g., 150 Gpa, and Poissons ratio, 0.28), and b) substrate geometry divided into sites corresponding to lithography fields to result in site-based geometry 505. The wafer geometry includes front and back surface NT 507 and thickness 508. Chuck parameters 510 (in the exemplary case, lithography chuck) are a second input category, which may include chuck design 511 such as the pin top size (for example 0.2×0.2 mm), pin spacing (for example 2 mm), pressure (e.g., 80 kPa), and chuck ceramic material properties 513. Inputs to the finite element model are varied depending on the parameter under study. The model simulates the interaction of the wafer back surface NT with the lithography pin chuck and how it affects the front surface NT while the wafer is on the vacuum chuck (termed "post-chucking). The outputs of the finite element model include, on a site-by-site basis: out-of-plane distortion (OPD) 520, which is correlated with defocus 525 (a parameter described by leveling verification test (LVT) data. LVT is described in US patent publication 20090135389, which is hereby incorporated by reference), and in-plane distortion (IPD) 530, which is correlated with overlay 535. Both defocus and overlay are observed at the lithography scanner and generally calculated at each lithography site. Post-processing 540 of the FE output data is performed to yield the calculated overlay error. Details of methods for calculating overlay are found in the previously incorporated paper by Turner et al. The outputs may also include the post-chucking front surface NT resulting from the interaction of the back surface NT with the lithography chuck.

Figure 6:
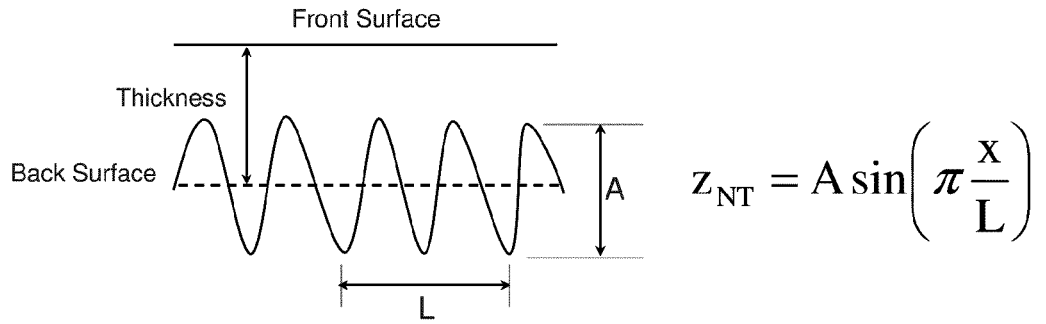
FIG. 6 illustrates an analytical model for an assumed ideal sinusoidal back wafer surface.

FIG. 6 illustrates an analytical model for an assumed ideal sinusoidal back wafer surface. This model results from the fundamental mechanics of plate theory. The front surface topography is calculated assuming the back surface of the wafer is completely flattened by the vacuum chuck. There is excellent correlation between the FE model and the analytical model for NT spatial wavelengths of 2 mm and above: for shorter spatial wavelengths, complex shear deformations become important, which are included in the FE model but not in the analytical model. Therefore the two models diverge for the short spatial wavelengths. The correlation between the two models is further validation of the FE analysis.

Figure 8:
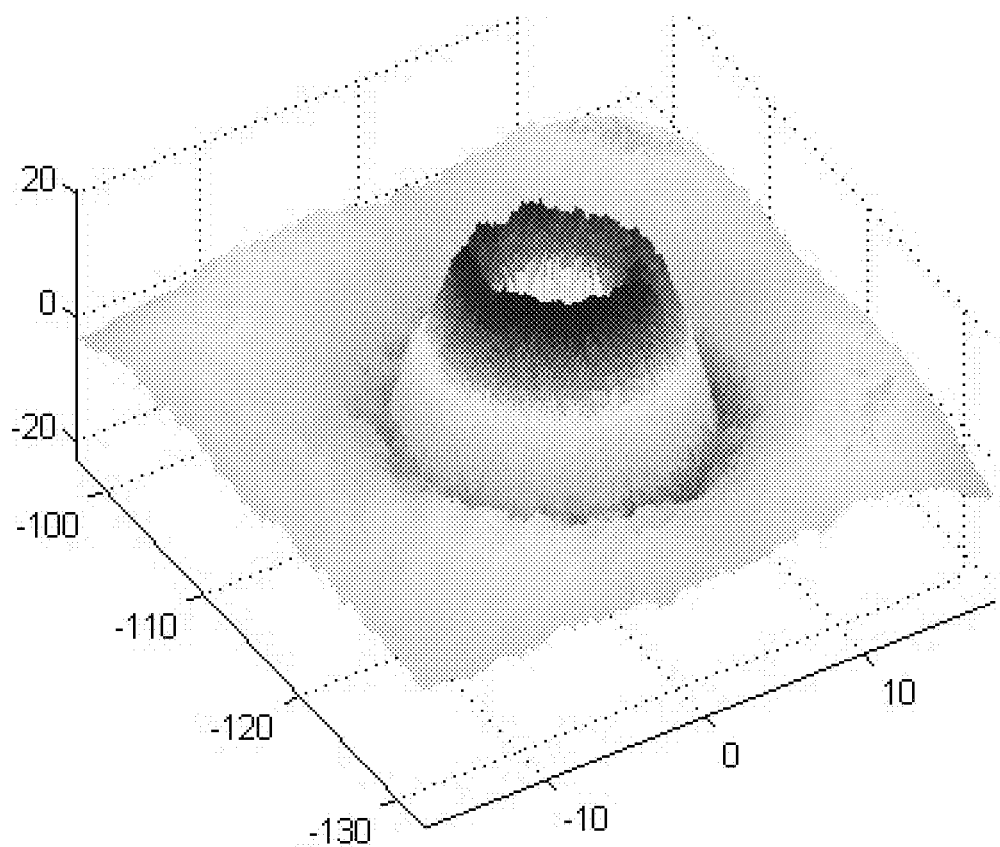
FIG. 8 illustrates an epi pin defect.

FIG. 7 shows exemplary FE modeling results of the effects of backside NT on frontside topography while chucked, for case 1 (FIG. 7a) and case 2 (FIG. 7b). For case 1, the backside topography is smaller than the frontside topography before chucking, and in this case the peak-to-valley (PV) topography of the front surface while chucked is affected very little. In contrast, for case 2, the backside NT is larger than the front surface topography before chucking. In this case, the chucked front surface is greatly affected by the backside NT. An example of an often-encountered large PV backside NT feature is an epi pin defect (illustrated in FIG. 8), a topography feature caused during an epi deposition process.

Figure 9:
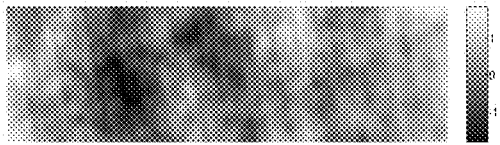
FIG. 9 illustrates front side In-Plane Distortion (IPD) (calculated using the FE model) corresponding to back surface NT.
Figure 9:
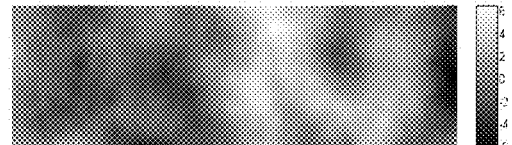
Figure 9:
Figure 9:
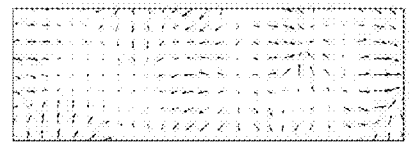

FIG. 9 illustrates front side IPD (calculated using the FE model) corresponding to back surface NT. Clearly, if backside NT can be quantified and controlled, overlay errors can be reduced and yield improved. If, by way of example, 5% of lithography sites are over epi pin defects, large PV NT features which will result in IPD and overlay error (and lower yield), then the potential exists to improve yield by an equivalent amount by controlling the epi pin NT.

System Considerations

The inventive methods or portions thereof may be computer-implemented. The computer system may include a processor (e.g. a processor core, a microprocessor, a computing device, etc), a main memory and a static memory, which communicate with each other via a bus. The machine may further include a display unit that may comprise a touchscreen, or a liquid crystal display (LCD), or a light emitting diode (LED) display, or a cathode ray tube (CRT). As shown, the computer system also may include a human input/output (I/O) device (e.g. a keyboard, an alphanumeric keypad, etc), a pointing device (e.g. a mouse, a touch screen, etc), a drive unit (e.g. a disk drive unit, a CD/DVD drive, a tangible computer readable removable media drive, an SSD storage device, etc), a signal generation device (e.g. a speaker, an audio output, etc), and a network interface device (e.g. an Ethernet interface, a wired network interface, a wireless network interface, a propagated signal interface, etc).

The drive unit may include a machine-readable medium on which is stored a set of instructions (i.e. software, firmware, middleware, etc) embodying any one, or all, of the methodologies described above. The set of instructions is also shown to reside, completely or at least partially, within the main memory and/or within the processor. The set of instructions may further be transmitted or received via the network interface device over the network bus.

It is to be understood that embodiments of this invention may be used as, or to support, a set of instructions executed upon some form of processing core (such as the CPU of a computer) or otherwise implemented or realized upon or within a machine- or computer-readable medium. A machine-readable medium includes any mechanism for storing or transmitting information in a form readable by a machine (e.g. a computer). For example, a machine-readable medium includes read-only memory (ROM); random access memory (RAM); magnetic disk storage media; optical storage media; flash memory devices; electrical, optical, acoustical or other form of propagated signals (e.g. carrier waves, infrared signals, digital signals, etc); or any other type of media suitable for storing or transmitting information.

As device geometries shrink, lithographic overlay accuracy must improve. To develop better correction strategies (including site-based NT control) for chucking-induced errors, one source of overlay errors and yield limiting, a first step is quantification of chucking-induced IPD. The methodology and system disclosed herein provides lithography site-based quantification of backside NT and FE modeling of corresponding chucking-induced IPD and overlay error.

It is not expected that the present invention be limited to the exact embodiments disclosed herein. Those skilled in the art will recognize that changes or modifications may be made without departing from the inventive concept. By way of example, other methods of obtaining the NT than high pass filtering may be used. The scope of the invention should be construed in view of the claims.

With this in mind, we claim:

1. A method for evaluating metrological characteristics of a semiconductor substrate, the method comprising:
    measuring, utilizing an optical measurement system, nanotopography (NT) of at least one of: a front surface, a back surface, and a thickness of said substrate;
    dividing said substrate into evaluation areas/sites;
    modeling effects of said NT on lithography process parameters utilizing a three-dimensional (3-D) finite element model, wherein said 3-D finite element model utilizes wafer parameters and chuck parameters as inputs and simulates wafer response on a lithography chuck during lithography processing, and wherein outputs from said 3-D finite element model include an out-of-plane distortion (OPD) and an in-plane distortion (IPD) on an individual site basis.

2. The method of claim 1, wherein said measuring NT of front and back surface of said substrate comprises:
    retaining said substrate in a free state; and
    performing optical measurements at points on said front and back surface of said substrate to produce surface data; and
    obtaining said NT from said surface data.

3. The method of claim 2, wherein;
    said performing optical measurements at points on said front and back surface of said substrate comprises performing optical measurements at points on a front surface and a back surface of said substrate to produce front surface data and back surface data; and
    said obtaining said NT from said surface data comprises filtering at least one of: said front surface data, said back surface data, and said thickness using a high pass filter to obtain filtered surface data, said filtered surface data representing nanotopography (NT) of at least one of: said front surface, said back surface, and said thickness of said substrate.

4. The method of claim 3, wherein said high pass filter is a Double Gaussian (DG) filter.

5. The method of claim 3, further comprising:
    characterizing said substrate based at least in part on said filtered surface data for said evaluation areas/sites.

6. The method of claim 5, wherein said evaluation areas/sites are equivalent to lithography scanner fields.

7. The method of claim 5, further comprising
    computing metrics values including Peak-to-Valley (PV) range and root mean square (RMS) metrics of said NT at said front surface, said back surface, and said thickness of said substrate for each said evaluation area/site.

8. The method of claim 7 adapted to characterize the fitness of said substrate to an integrated circuit process flow, further comprising:
    comparing said metric values to a threshold determined based at least in part on said process flow.

9. The method of claim 1, wherein:
    said wafer parameters include
        site-based substrate geometry comprising front and back surface NT and thickness; and
        silicon material properties.

10. The method of claim 1, wherein:
    said chuck parameters include
        chuck design comprising at least one of: pin size, pin spacing, and vacuum rings;
        pressure; and
        ceramic material properties.

11. The method of claim 1, further including:
    comparing said out-of-plane distortion (OPD) to defocus data; and
    comparing said in-plane distortion (IPD) to overlay data.

12. A system for evaluating metrological characteristics of a semiconductor substrate comprising;
    an optical measurement system configured to measure nanotopography (NT) of at least one of: a front surface, a back surface, and a thickness of said substrate; and
    a data analysis system including a computer configured to:
        divide said substrate into evaluation areas/sites;
        model effects of said NT on lithography process parameters utilizing a three-dimensional (3-D) finite element model, wherein said 3-D finite element model utilizes wafer parameters and chuck parameters as inputs and simulates wafer response on a lithography chuck during lithography processing, and wherein outputs from said 3-D finite element model include an out-of-plane distortion (OPD) and an in-plane distortion (IPD) on an individual site basis.

13. The system of claim 12, wherein said optical measurement system is configured to retain said substrate with only point contacts that hold the substrate in a vertical position, thereby maintaining said substrate in a free state.

14. The system of claim 13, wherein said optical measurement system is further configured to;
    perform optical measurements at points on a front surface and a back surface of said substrate simultaneously to produce front and back surface data;
    obtain thickness of said substrate from said front and back surface data by adding the front and back surface data; and obtain front and back surface NT from said front and back surface data using a high pass filter to obtain filtered surface data.

15. The system of claim 14, wherein said high pass filter is a Double Gaussian (DG) filter.

16. The system of claim 14, wherein said computer is configured to:
characterize said substrate based at least in part on said filtered surface data for said evaluation area sites.

17. The system of claim 16, wherein said evaluation area sites are equivalent to lithography scanner fields.

18. The system of claim 16, wherein said computer is configured to compute metrics values including Peak to Valley (PV) range and root mean square (RMS) metrics of said NT at said front surface, said back surface, and said thickness of said substrate for each said evaluation area site.

19. The system of claim 18, wherein said computer is configured to characterize the fitness of said substrate to an integrated circuit process flow by comparing said metrics values to a threshold determined based at least in part on said process flow.

20. The system of claim 12, wherein:
said wafer parameters include
site-based substrate geometry comprising front and back surface NT and thickness; and
silicon material properties; and wherein said chuck parameters include
chuck design comprising at least one of: pin size, pin spacing, and vacuum rings;
pressure; and
ceramic material properties.

21. The system of claim 12, wherein said computer is further configured to:
compare said OPD to defocus data; and
compare said IPD to overlay data.

* * * * *